United States Patent
Fujii

(10) Patent No.: US 6,699,225 B2
(45) Date of Patent: Mar. 2, 2004

(54) MIXING/CHARGING PORT FOR MEDICAL TREATMENT

(75) Inventor: Ryoji Fujii, Hiroshima (JP)

(73) Assignee: JMS Co., Ltd., Hiroshima (JP)

(*) Notice: Subject to any disclaimer, the term of this patent is extended or adjusted under 35 U.S.C. 154(b) by 30 days.

(21) Appl. No.: 09/963,834

(22) Filed: Sep. 25, 2001

(65) Prior Publication Data

US 2002/0038106 A1 Mar. 28, 2002

(30) Foreign Application Priority Data

Sep. 26, 2000 (JP) .......................... 2000-292024

(51) Int. Cl.⁷ .................. A61M 5/14; A61M 37/00; A61M 31/00
(52) U.S. Cl. ..................... 604/256; 604/86; 604/95
(58) Field of Search ................. 604/82, 83, 86, 604/87, 88, 89, 90, 91, 167.01, 167.02, 167.03, 167.04, 200, 201, 205, 244, 246, 256, 905; 137/845, 851; 251/149.1

(56) References Cited

U.S. PATENT DOCUMENTS

| 4,981,140 A | 1/1991 | Wyatt |
| 5,135,489 A | 8/1992 | Jepson et al. |
| 5,178,607 A | 1/1993 | Lynn et al. |
| 5,199,948 A | 4/1993 | McPhee |
| 5,203,775 A | 4/1993 | Frank et al. |
| 5,279,571 A | 1/1994 | Larkin |
| 5,306,265 A | 4/1994 | Ragazzi |
| 5,324,256 A | 6/1994 | Lynn et al. |
| 5,417,673 A | 5/1995 | Gordon |
| 5,531,672 A | 7/1996 | Lynn |
| 5,603,706 A | 2/1997 | Wyatt et al. |
| 5,989,216 A | 11/1999 | Johnson et al. |
| 6,213,973 B1 | 4/2001 | Eliasen et al. |
| 6,468,251 B1 * | 10/2002 | Yamanaka et al. .......... 604/256 |

FOREIGN PATENT DOCUMENTS

| EP | 0 499 401 A | 8/1992 |
| EP | 0 783 899 A2 | 7/1997 |
| EP | 1 040 845 A | 10/2000 |
| JP | 3-62113 | 9/1991 |
| JP | 4-200566 | 7/1992 |
| JP | 3066107 | 11/1999 |
| WO | 95/03841 A | 2/1995 |
| WO | 99/24108 A | 5/1999 |

* cited by examiner

Primary Examiner—Brian L. Casler
Assistant Examiner—Mark K. Han
(74) Attorney, Agent, or Firm—Merchant & Gould P.C.

(57) ABSTRACT

A mixing/charging port for medical treatment capable of cleanly wiping out a residual liquid, residual blood, or the like. The mixing/charging port includes a disk-like valve having an insertion hole at the center, a seating for supporting a lower part of the periphery of the valve, and a cover for restraining the valve. A fitting hole defined by an inner edge portion of the cover works as an anchor for anchoring an insertion member to the mixing/charging port, the thickness of the center of the valve is larger than the thickness of the periphery of the valve, and the thickness of the edge portion of the cover provided with the fitting hole substantially corresponds to the difference between the thickness of the center of the valve and the thickness of the periphery of the valve.

2 Claims, 5 Drawing Sheets

MIXING/CHARGING PORT FOR MEDICAL TREATMENT

BACKGROUND OF THE INVENTION

1. Field of the Invention

The present invention relates to a mixing/charging port for medical treatment, which is placed on a medical instrument to make it easy and reliable to mix/charge solutions from the outside of a feeding passage or, on the other hand, to collect solutions from the inside of the feeding passage.

2. Description of the Prior Art

In infusing a drug solution or transfusing blood into a patient, it is often necessary to provide a main feeding passage with a side-infusing line in order to mix/charge different kinds of drug solutions or to collect the liquid flowing in the feeding passage as a sample. Conventionally, in this case, a feeding passage of an infusion set provided with a rubber mixing/charging port (cock) for piercing by needles is used and solutions are mixed/charged by piercing the mixing/charging port with an injection needle, etc.

However, in such a method, when piercing the site other than the predetermined piercing site of the mixing/charging port with the needle, the liquid may leak from the site. Another problem is that the injection needle may be contaminated due to a working error, etc. In order to fix and hold a luer, etc. to be inserted ("an insertion member" will be referred to hereinafter), recently, the mixing/charging port capable of holding an insertion member has been considered. An example includes a mixing/charging port equipped with a valve that opens when a male luer located at the tip of a syringe is inserted into the mixing/charging port to push the valve and which closes by itself when the luer is pulled out from the mixing/charging port.

However, in such a mixing/charging port, it is necessary to hold a luer at the mixing/charging port regardless of the state in which the valve is inserted (i.e., valve opens) or the state in which the valve is pulled out (i.e., valve closes). Therefore, there are the following various problems. More specifically, first, it is necessary to deepen a luer receiving part of the mixing/charging port. With such a shape, it is difficult to remove the liquid leaking from the valve, which easily may be become unsanitary. Furthermore, in the mixing/charging port having such a deep luer receiving part, the liquid may begin to be mixed/charged in a state in which the luer is not sufficiently inserted into the valve. In this case, if the amount of drug solution to be mixed/charged is small, the administration of an effective amount of drug solution may not be carried out. Secondly, the structure of the valve becomes complicated, which may lead to increasing cost. Furthermore, as the structure of the valve is more complicated, failures are more likely to occur, and the valve is more likely to be broken.

On the other hand, in the conventional simple-structured mixing/charging port (for example, a mixing/charging port merely equipped with a disk-like valve made of an elastic member having a slit), it was difficult to insert a luer of a syringe into the mixing/charging port. If possible, it was difficult to hold the syringe reliably at the mixing/charging port. This is because the conventional disk-like valve is formed of a material having a large elasticity and has a simple structure in which the thick main body is merely provided with a slit, so that the valve exhibits a large resistance when the luer is inserted into the valve, and the valve is deformed largely when the valve holds the luer. However, if the thickness of the elastic member is reduced or a material having a small elasticity is used in order to reduce the resistance when the luer is inserted, the backflow prevention effect of the valve is lowered, which may cause liquid leaking.

In order to solve the above-mentioned problems, there has been a proposal of a mixing/charging port for medical treatment having a simple structure and capable of reliably holding an insertion member, which includes a disk-like valve having an insertion hole at the center, a seating for supporting the lower part of the periphery of the valve with the center of the rear surface side of the valve left unsupported, a cover for restraining the valve by covering at least the upper part of the periphery of the valve with the center on the front surface side of the valve left uncovered, and an anchor means for anchoring the insertion member to the mixing/charging port by inserting the insertion member into the insertion hole and by using the edge portion of the cover provided with a fitting hole.

FIGS. 1A, 1B and 1C are projection drawings from three directions of an example of a conventional mixing/charging port for medical treatment. That is, FIG. 1A is a longitudinal sectional view of a mixing/charging port; FIG. 1B is a cross sectional view of the mixing/charging port along line I—I in FIG. 1A; and FIG. 1C is a plan view of the mixing/charging port, respectively.

In FIG. 1, reference numeral 1 denotes a disk-like valve, 2 denotes a cover, and 3 denotes an insertion hole. Furthermore, reference numeral 5 denotes an annular rib, 6 denotes a fitting hole, 7 denotes a seating, 8 denotes a passage, and 9 denotes a hook. In this structure, the valve 1 is sandwiched between the hook 9 of the cover 2 and the annular rib 5.

However, in the above-mentioned mixing/charging port for medical treatment, there has been a problem in that since a difference in level unavoidably occurs between the valve and the cover for restraining the valve, when a drug solution or blood leaks onto the upper part of the valve, it cannot be wiped out cleanly.

FIGS. 2A and 2B are views showing an example of the shape of the valve 1 of a conventional mixing/charging port for medical treatment. FIG. 2A is a plan view thereof; and FIG. 2B is a cross sectional view along line I—I in FIG. 2A.

Since the thickness of the center of the valve 1 is the same as that of the periphery of the valve 1 as shown in FIG. 2, a certain difference in level 10 unavoidably occurs at the edge portion of the cover 2 provided with a fitting hole 6 as shown in FIG. 3. Therefore, when a residual liquid, residual blood, or the like is wiped out, there is some liquid or blood left due the presence of the difference in level 10, thus making it impossible to wipe out the residual liquid, residual blood, etc. cleanly.

If the residual liquid, residual blood, or the like is contaminated with the other drug solution, it adversely affects the human body. In order to avoid this, the mixing/charging port should not be reused, and thus the reusability is reduced radically. In particular, it has strongly been required to wipe out such residues easily from the viewpoint of avoiding infection by infectious diseases by residual blood.

SUMMARY OF THE INVENTION

With the foregoing in mind, it is an object of the present invention to provide a mixing/charging port for medical treatment capable of cleanly wiping out a residual liquid, residual blood, or the like.

In order to achieve the above-mentioned object, a mixing/charging port for medical treatment of the present invention includes: a disk-like valve having an insertion hole at the center, a seating for supporting a lower part of the periphery of the valve with the center of a rear surface side of the valve left unsupported, and a cover for restraining the valve by covering at least an upper part of the periphery of the valve with the center of a front surface side of the valve left uncovered, wherein a fitting hole defined by an inner edge portion of the cover works as an anchor for anchoring an insertion member to the mixing/charging port in a way in which the insertion member is fitted to the fitting hole when the insertion member is inserted into the insertion hole; and the thickness of the center of the valve is larger than the thickness of the periphery of the valve, and the thickness of the edge portion of the cover provided with the fitting hole substantially corresponds to the difference between the thickness of the center of the valve and the thickness of the periphery of the valve.

According to such a configuration, the difference in level between the cover and the valve, which occurs at the edge portion of the cover provided with the fitting hole, can be avoided. Therefore, even if the drug solution or blood leaks onto the upper part of the valve due to carelessness or a working error, etc., such liquid or blood can easily be wiped out. Thus, it is possible to prevent the attachment of a drug solution, etc., infection by infectious disease, or the like before it happens.

Furthermore, in the mixing/charging port for medical treatment of the present invention, it is preferable that the difference between the thickness of the center of the valve and the thickness of the periphery of the valve is 60% or more and 80% or less with respect to the thickness of the edge portion of the cover. The thickness of the center of the valve slightly is increased when the valve is pressed down by the cover. Therefore, if the difference between the thickness of the center of the valve and the thickness of the periphery of the valve is 80% or more with respect to the thickness at the edge portion of the cover, the center of the valve is located higher than the cover when the insertion member is inserted into the valve, and thus a difference in level occurs. On the other hand, if the difference between the thickness of the center of the valve and the thickness of the periphery of the valve is 60% or less with respect to the thickness at the edge portion of the cover, when the insertion member is inserted into the valve, the center of the valve is located lower than the cover, and thus a difference in level occurs. In either case, it is difficult to wipe out a residual liquid.

Furthermore, in the mixing/charging port for medical treatment according to the present invention, it is preferable that the thickness of the center of the valve is 100% or more and 130% or less with respect to the thickness of the periphery of the valve. It is preferable because too large thickness of the center of the valve makes it difficult to insert the insertion member into the valve. Furthermore, the elasticity of some materials used for the valve may make it difficult to hold the insertion member reliably. On the other hand, when the above-mentioned value is less than 100%, a residual liquid tends to be collected at the center of the valve.

DESCRIPTION OF THE PREFERRED EMBODIMENTS

Figure 1C:
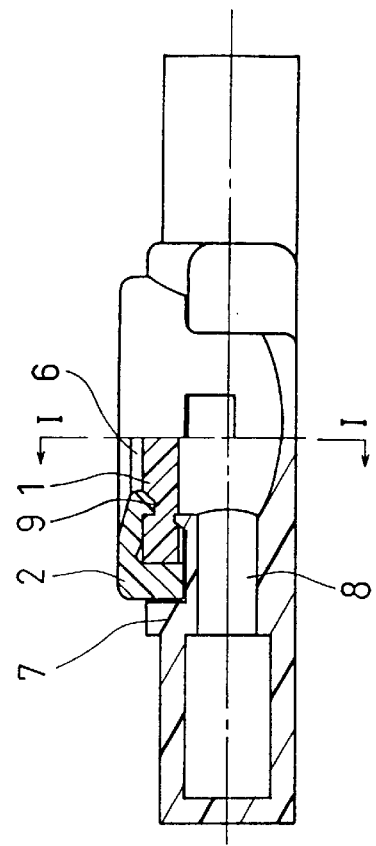
FIG. 1C is a conventional plan view of the mixing/charging port.
Figure 1A:
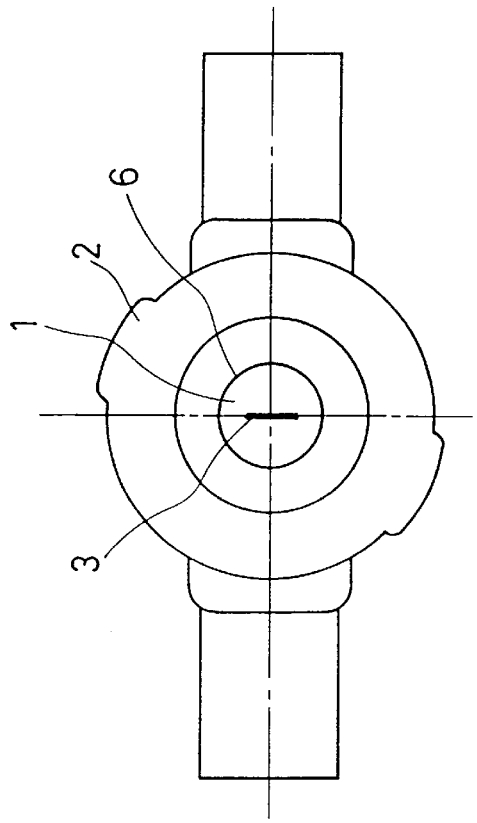
FIG. 1A is a longitudinal sectional view of a conventional mixing/charging port.
Figure 1B:
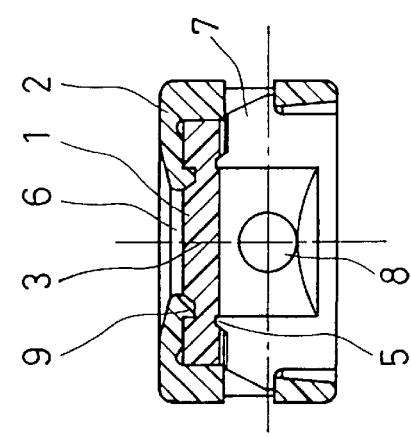
FIG. 1B is a cross sectional view of the mixing/charging port along line I—I in FIG. 1A.
Figure 2A:
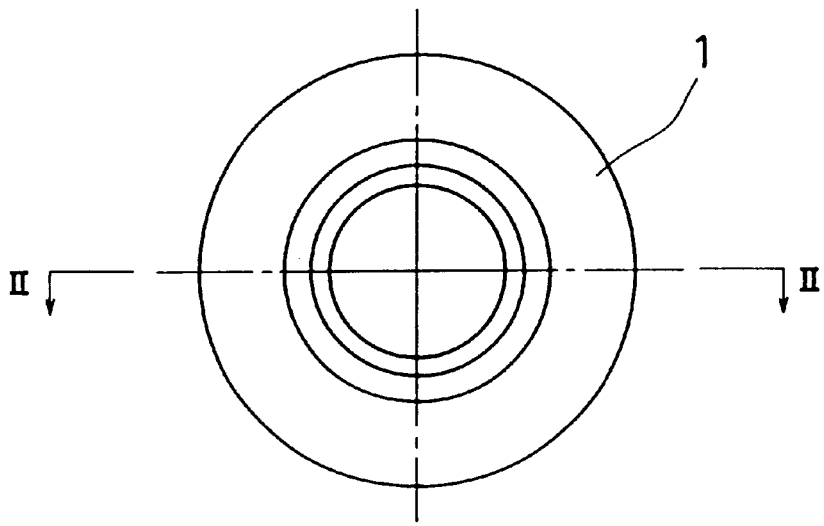
FIG. 2A is a plan view showing a configuration of a valve of a mixing/charging port for medical treatment.
Figure 2B:
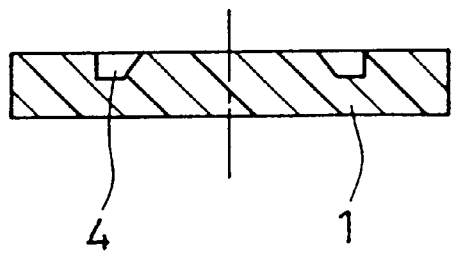
FIG. 2B is a cross sectional view along line I—I in FIG. 2A.
Figure 3:
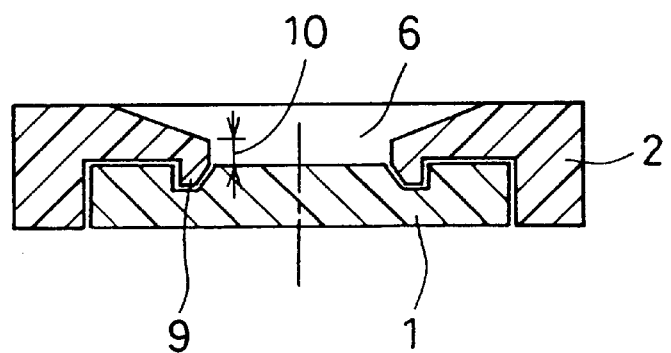
FIG. 3 is a sectional view showing a state in which a valve is placed in a mixing/charging port for medical treatment of the prior art.
Figure 4:
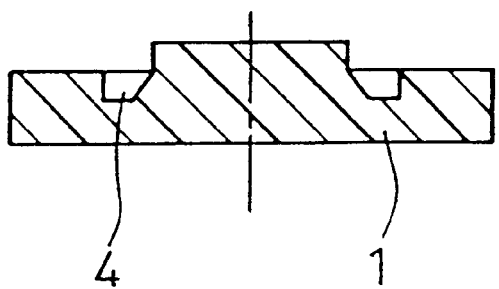
FIG. 4 is a sectional view showing a configuration of a mixing/charging port for medical treatment of the present invention.

Hereinafter, the mixing/charging port for medical treatment of the present invention will be described by way of embodiments with reference to the accompanying drawings. FIG. 4 is a sectional view showing a valve 1 of a mixing/charging port for medical treatment of this embodiment according to the present invention. The valve of FIG. 4 is the same as that of FIG. 2 in that the valve has a disk-like shape. However, the valve of FIG. 4 is different from that of FIG. 2 in that the thickness of the center of the valve 1 is larger than the thickness of the periphery of the valve in FIG. 4. A valve cutaway part 4 forms a boundary between the center of the valve and the periphery of the valve.

Figure 5:
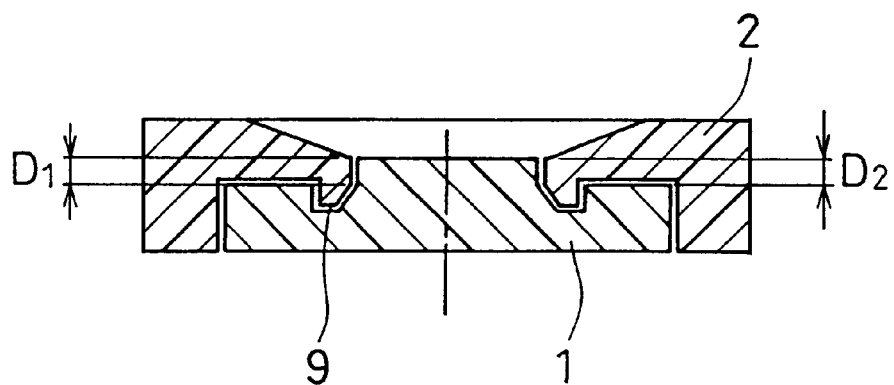
FIG. 5 is a sectional view showing a state in which a valve is placed in a mixing/charging port for medical treatment of the present invention.

FIG. 5 is a sectional view showing a state in which the valve 1 is placed in the mixing/charging port by the use of the cover 2. As shown in FIG. 5, since the thickness of the center of the valve is large, the valve 1 is so placed as to cover the fitting hole 6 of the cover 2. In other words, the thickness of the edge portion of the cover 2 provided with the fitting hole 6 is made to correspond to the difference between the thickness of the center of the valve 1 and the thickness of the periphery of the valve 1, it is possible to prevent a difference in level from occurring between the cover 2 and the valve 1.

According to such a configuration, the difference in level occurring between the cover 2 and the valve 1 can be avoided. Therefore, even if the drug solution or blood leaks out onto the upper surface of the valve 1, it can be wiped out easily. Thus, it is possible to prevent residual liquid, residual blood, or the like from collecting due to the presence of the difference in level before it leaks.

Furthermore, since the residual liquid, residual blood or the like can be wiped out cleanly, even if a drug solution or blood leaks out onto the upper part of the valve due to carelessness, a working error, etc. at the time of transfusing blood or infusing a drug solution to the vessle of a patient, such liquid or blood can easily be wiped out. Thus, it is possible to carry out the medical treatment sanitarily and safely.

Furthermore, since the thickness of the center of the valve 1 is relatively larger than the thickness of the periphery of the valve, the reaction force by the elasticity of the valve 1 becomes higher, when the insertion member is inserted while pressing down the valve 1. Therefore, it may be difficult to insert the insertion member deeply or to hold the insertion member.

It is confirmed from the experiments that the above-mentioned problems do not occur when $D_2$ is 60% or more and 80% or less of $D_1$ as shown in FIG. 5, wherein $D_1$ denotes a thickness of the edge portion of the cover 2 and $D_2$ denotes a difference between the thickness of the center of the valve 1 and the thickness of the periphery of the valve 1. Herein, this result was obtained when the experiment was carried out by using a synthetic isoprene rubber as a material for the valve 1. However, a material for the valve 1 is not particularly limited to this alone, and other materials can be used. More specifically, in a case where a thermoplastic elastomer having a rigidity of 20 to 55 in accordance with JIS-A, for example, a silicone rubber, a natural rubber, a synthetic rubber such as butyl rubber, nitrile rubber, etc. is used, the same effect can be obtained.

The invention may be embodied in other forms without departing from the spirit or essential characteristics thereof. The embodiments disclosed in this application are to be considered in all respects as illustrative and not limitative, the scope of the invention is indicated by the appended claims rather than by the foregoing description, and all changes which come within the meaning and range of equivalency of the claims are intended to be embraced therein.

What is claimed is:

1. A mixing/charging port for medical treatment comprising a disk-like valve having an insertion hole at the center, a seating for supporting a lower part of the periphery of the valve with the center of a rear surface side of the valve left unsupported, and a cover for restraining the valve by covering at least an upper part of the periphery of the valve with the center of a front surface side of the valve left uncovered, wherein:

a fitting hole defined by an inner edge portion of the cover works as an anchor for anchoring an insertion member to the mixing/charging port in a way in which the insertion member is fitted to the fitting hole when the insertion member is inserted into the insertion hole, the inner edge portion comprising an annular wall having a height and an upper edge; and the thickness of the center of the valve is larger than the thickness of the periphery of the valve, where the difference between the thickness of the center of the valve and the thickness of the periphery of the valve is 60% or more and 80% or less with respect to the height of the annular wall of the inner edge portion, whereby the upper edge of the annular wall of the inner edge portion corresponds substantially to an upper surface of the center of the valve.

2. The mixing/charging port for medical treatment according to claim 1, wherein the thickness of the center of the valve is 100% or more and 130% or less with respect to the thickness of the periphery of the valve.

* * * * *